United States Patent [19]

Horecker

[11] 4,389,343
[45] Jun. 21, 1983

[54] IMMUNOPOTENTIATING PEPTIDES FROM THYMUS

[75] Inventor: Bernard L. Horecker, New York, N.Y.

[73] Assignee: Hoffmann-La Roche Inc., Nutley, N.J.

[21] Appl. No.: 334,420

[22] Filed: Dec. 24, 1981

[51] Int. Cl.$^3$ ............................................. C07C 103/52
[52] U.S. Cl. ............................................. 260/112.5 R
[58] Field of Search ................................. 260/112.5 R

[56] References Cited

U.S. PATENT DOCUMENTS 4,010,148  3/1977  Goldstein .................... 260/112.5 R
4,082,737  4/1978  McGregor et al. .......... 260/112.5 R
4,128,637  12/1978  Naylor et al. ................ 260/112.5 R

OTHER PUBLICATIONS

Goldstein, *Nature*, 247, 1974, pp. 11–14.
Yi-Feng Jin, Chem. Abstr., 93: 181280e, (1980).

*Primary Examiner*—Delbert R. Phillips
*Assistant Examiner*—F. T. Moezie
*Attorney, Agent, or Firm*—Jon S. Saxe; George M. Gould; Peter R. Shearer

[57] ABSTRACT

Novel polypeptides, designated thymosin $\beta_8$ and thymosin $\beta_9$, have been isolated from calf thymus and their amino acid sequences established. These peptides are active agents for restoring or stimulating immune function, especially for opportunistic infection.

4 Claims, No Drawings

IMMUNOPOTENTIATING PEPTIDES FROM THYMUS

BACKGROUND OF THE INVENTION

Several polypeptides present in the thymus gland have been implicated to play an important role in the development and maintenance of immunological competence in animals, including man. The importance of the immune system in the defense against cancer and tumor cells is now widely recognized. In recent years, a few polypeptides shown to be able to stimulate maturation, differentiation and function of T cells have been isolated from calf thymus.

Particularly a heat-stable fraction has been prepared from calf thymus extracts and designated Thymosin Fraction 5. Studies have shown that Thymosin Fraction 5 is a potent immunopotentiating preparation and that it can act in lieu of the thymus gland to reconstitute immune functions in thymic deprived or immunodeprived individuals. Peptides which have been isolated from Thymosin Fraction 5 include thymosin $\alpha_1$, an acidic peptide containing 28 amino acid residues, the structure of which has been described in U.S. Pat. No. 4,079,127, and thymosin $\beta_4$ containing 44 amino acid residues [Low, T.L.K., et al., Proc. Nat. Acad. Sci. 78, 1162–1166 (1981)],

SUMMARY OF INVENTION

Two new polypeptides, designated thymosin $\beta_8$ and thymosin $\beta_9$, respectively, have been isolated and their amino acid sequences established. Thymosin $\beta_8$, isolated from calf thymus Fraction 5, has a mass of 4,518 daltons and contains 39 amino acid residues, 31 of which are identical to the corresponding amino acid residues in thymosin $\beta_4$ isolated from the same source. The NH$_2$-terminus of thymosin $\beta_8$ is acetyl alanine, compared with acetyl serine in thymosin $\beta_4$. Thymosin $\beta_9$, isolated from fresh frozen calf thymus by a procedure that minimized proteolysis, is identical to thymosin $\beta_8$ except for the presence of an additional dipeptide, —Ala—LysOH, at the COOH-terminus. It has a mass of 4,717 daltons and 32 of its 41 amino acids are identical to those of thymosin $\beta_4$. Thymosin $\beta_8$ and thymosin $\beta_9$ are useful as agents for restoring or stimulating immune function, and thus are especially useful for treating or preventing opportunistic infections.

DETAILED DESCRIPTION OF THE INVENTION

The present invention relates to the isolation and, purification and characterization of novel polypeptides endogenous to calf thymus and having the formula:

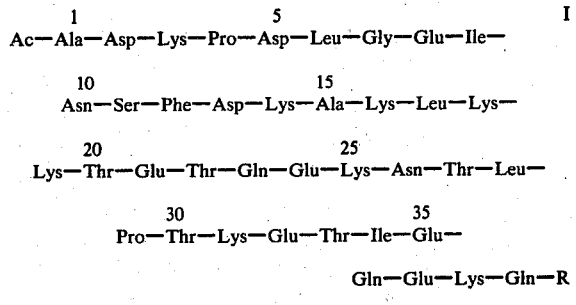

wherein Ac represents N-acetyl and R represents —OH or —Ala—Lys—OH and the pharmaceutically acceptable acid addition salts or base salts thereof.

The compounds of formula I particularly include the compound designated thymosin $\beta_8$ with a molecular weight of 4,518 daltons and having the sequence:

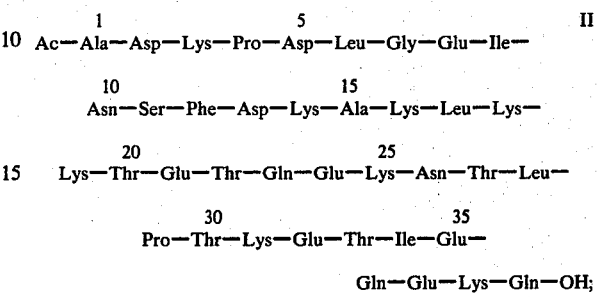

and the compound designated thymosin $\beta_9$ with a molecular weight of 4,717 daltons and having the sequence:

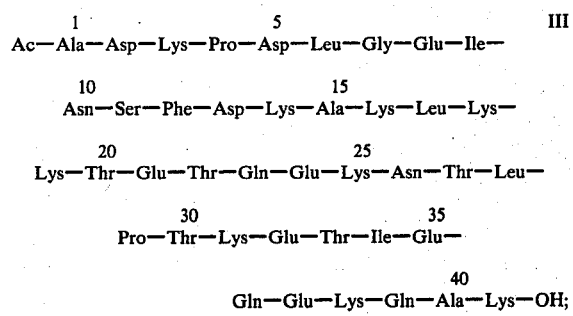

Compounds of formula II and III, i.e. compounds of formula I, have been obtained essentially free of other biologically endogenous proteinacious substances.

Compounds of formula I may be prepared from any animal tissue containing compounds associated with Thymosin Fraction 5. Among such tissues there are included the thymus and spleen. Sources of such tissue include calf, pig, sheep and similar mammalian species. The preferred source of compounds of formula I is calf thymus.

Thymosin Fraction 5 may be isolated from calf thymus by the procedure of Goldstein, et al., Proc. Nat. Acad. Sci. 69, 1800–1803 (1972), and the compound of formula II may be prepared from Thymosin Fraction 5 by methods well known in the art and purified to be essentially free of other proteinacious substances as by conventional chromatographic methods, such as by a combination of ion-exchange chromatography and gel filtration, as by the methods described by Goldstein, et al., Proc. Nat. Acad. Sci. USA 74, 725–729 (1977), Low, et al., J. Biol. Chem. 254, 981–986 (1979) and Low, et al., Proc. Nat. Acad. Sci. USA 78, 1162–1166 (1981), or by preparative isoelectric focusing and high pressure liquid chromatography (HPLC), as described herein.

It is preferred that the compound of formula II be separated conventionally from Thymosin Fraction 5 using preparative isoelectric focusing, with the proteins recovered therefrom being purified by HPLC. By such a procedure, for example, 1.2 grams of Thymosin Fraction 5 provided 16 mg of thymosin $\alpha_1$, 16 mg of thymosin $\beta_4$ and 1 mg of the compound of formula II.

The isoelectric point for the compound of formula II was pH 4.62.

It was surprisingly observed on the one hand that the compound of formula II did not occur significantly in frozen preparations of fresh calf thymus tissue, which preparations had been extracted in their frozen state while simultaneously being treated in a novel manner with an anti-proteolytic agent. While on the other hand, it was observed that the compound of formula III did not occur significantly in preparations of Thymosin Fraction 5 prepared as described above without treatment with an anti-proteolytic agent. It would appear, therefore, that the compound of formula II is a product occurring by endogenous proteolytic modification of the compound of formula III.

For the preparation of the compound of formula III, it is preferred that a novel procedure be used, which procedure employs in a novel way an anti-proteolytic agent. In particular, calf thymus tissue is collected at the time of slaughter of the calf, providing thereby fresh tissue, which is immediately frozen by any conventional method as by use of liquid $N_2$. The tissue may be stored in its frozen state as, for example, under liquid $N_2$ or in dry ice until further use.

In preparing the tissue in order to obtain the compound of formula III, it is essential that the frozen tissue be treated with the anti-proteolytic agent while the tissue is frozen. For example, the frozen tissue may be pulverized in the presence of the anti-proteolytic agent or separately pulverized while frozen and the resulting frozen powder added to a solution of the ice cold anti-proteolytic agent with conventional mechanical agitation. After treatment of the frozen tissue with the anti-proteolytic agent, the treated tissue may then be submitted to any conventional isolation and purification processes for separating polypeptides, as, for example, preparative isoelectric focusing, chromatography, electrophoresis, ultrafiltration and the like. The preferred isolation procedure is by conventional use of ultrafiltration and HPLC, especially HPLC with a reverse phase hydrophobic resin.

Any reverse phase hydrophobic resin may be employed in a conventional manner in the HPLC isolation. Among such resins there are included, for example, a hydrocarbon ($C_8$ to $C_{18}$) on any inert matrix such as silica gel, glass, polysaccharides and the like, which matrix is inert to the eluting agent being employed. The preferred resin is a straight chain $C_{18}$ hydrocarbon bonded to silica gel or glass beads. The eluting agent may be any miscible solvent eluting the selected peptides being isolated. For example, the eluting solvent for thymosin $\beta_8$ and thymosin $\beta_9$ may be solvents such as lower alkyl alcohols such as propanol, or nitriles such as acetonitrile or organic acids such as trifluoroacetic acid. The preferred solvent and eluting agent is propanol. The elution is carried out in a buffer, preferably in aqueous pyridine-formic acid. The isoelectric point for the compound of formula III is pH 5.14. The compound of formula III emerges in the preferred solvent from HPLC immediately after thymosin $\beta_4$ which was separated from the compound of formula III by converting thymosin $\beta_4$ to the sulfoxide using the method of Neumann, in *Methods of Enzymatic Analysis*, 25, 395 (1972).

The anti-proteolytic agent may be any guanidinium salt. Among such guanidinium salts there are included the organic acids such as acetic acid and the mineral acids such as the hydrohalides, i.e., hydrobromide, hydrochloride, hydrofluoride, hydroiodide, or thiocyanate. The preferred guanidinium salt is guanidine hydrochloride. The concentration of guanidinium salt in treatment of the tissue is not critical. It is preferred, however, that 3–6 M solution of the guanidium salt be used for treating the tissue and that about 3 to 9 volumes of the salt solution per gram of tissue be used. The concentration of the salt may be achieved by making the salt up in a solvent such as water or an aqueous buffer such as ammonium acetate or pyridine acetic acid or the like.

Particularly, for example, as one aspect of the invention, the polypeptide, thymosin $\beta_9$, may be isolated from frozen thymus tissue by a process which encompasses extraction of the polypeptide by the following steps:

(1) homogenizing the tissue in the presence of an ice cold aqueous solution containing an effective amount of guanidinium hydrochloride, (2) suspending the resulting homogenate in a pyridine-formic acid solution at about pH 4.0;

(3) centrifuging the resulting suspension and obtaining the resulting supernatant;

(4) ultrafiltering the resulting supernatant through ultrafilters having a molecular weight cut-off of 10,000 daltons;

(5) submitting the resulting filtrate to a chromatographic column utilizing a reverse phase hydrophobic resin;

(6) washing the resin pyridine-formic acid buffer solution of about pH 4.0;

(7) collecting the material eluting from said resin upon applying the same buffer containing 40% by volume n-propanol, and (8) isolating the polypeptides inclusive of thymosin $\beta_9$, from the resulting 40% n-propanol eluate of step (7) by high pressure liquid chromatography (HPLC) utilizing a reverse phase hydrophobic resin and eluting with a gradient of increasing concentrations of n-propanol from 0 to 40% by volume in the aforesaid buffer.

In step (8) above thymosin $\beta_9$ emerges from the HPLC immediately after thymosin $\beta_4$. In order to more completely separate thymosin $\beta_4$ from thymosin $\beta_9$, the eluate from step (8) containing the aforesaid polypeptides is collected and thymosin $\beta_4$ therein is converted to the sulfoxide using the method described earlier. The sulfoxide form of thymosin $\beta_4$ is then separated easily from thymosin $\beta_9$ by HPLC utilizing a reverse phase hydrophobic resin and eluting with a gradient of increasing concentrations of n-propanol from 0 to 40% by volume in the pyridine-formic acid buffer solution of about pH 4.0.

The purity of the polypeptides obtained by the procedures described herein may be determined conventionally by their homogeneity in any recognized conventional purification method, such as by ultracentrifuge, gel electrophoretic or chromatographic patterns. The identity of the purified polypeptide may be determined by any conventional amino acid analysis procedure or by sequencing.

Amino acid analyses of compounds of formula I, for example, were carried out with an Amino Acid Analyzer modified for derivitization with o-phthalaldehyde in accordance with the method of Benson, et al., Proc. Nat. Acad. Sci. 72, 619–622 (1975) and with a conventional fluorescence detector. Proline was determined with an amino acid analyzer employing a fluorescamine detection system after oxidation with N-chlorosuccinamide in accordance with the method of Weigele, et al., Biochem. Biophys. Res. Commun. 50, 352–356 (1973). Amino acids were released by carboxypeptidase A in a reaction carried out at room temperature for 2 hours in 0.2 M pyridine (pH 7.4) providing thereby a ratio of polypeptide to carboxypeptidase of 12.5:1 (w/w), and were analyzed by HPLC on a Ultrosphere-ODS column after prelabeling with o-phthalaldehyde in accordance with the method of Jones, et al., J. Liquid Chromatography 4, 565–586 (1981).

Enzymatic digestion of the compounds of formula I for sequence determinations were performed in conventional manner as by mild acid hydrolysis in 30 mM HCl at 105° C. for 15 hours as described by Schultz, Methods in Enzymology, Vol. XI, pp. 255–263 (1967), and/or by using tryspin and/or Staph aureus protease added to the purified polypeptides of formula I. Separation and analysis of the acid hydrolysates or enzymatic digests were performed conventionally by HPLC. The amino acid sequences of the separated peptides were determined by the manual Edman degradation procedures, Tarr et al., Methods in Enzymology, Vol. XLVII, 335–357 (1977). The data leading to the elucidation of the primary structures of the polypetides of formula I (designated hereafter as thymosin $\beta_8$ and thymosin $\beta_9$) are summarized in Tables I-III and FIGS. I and II.

Particularly, Tables I and II provide data of the amino acid composition of thymosin $\beta_8$ following digestion of thymosin $\beta_8$ with trypsin and digestion with Staph aureus protease V8. The peptide fragments resulting from trypsin digestion of thymosin $\beta_8$ are designated T1 through T5 in Table I. The peptide fragment T5 was further digested with Staph aureus protease V8 to provide peptides designated T5S1 and T5S2 in Table I. Dilute acid hydrolysis of T5S2 further provided peptide fragments designated T5S2H and T5S2H2 in Table I. The peptide fragments resulting from digestion of thymosin $\beta_8$ with Staph aureus protease V8 are designated S1 through S6 in Table II. There is provided in Table III data of the amino acid composition of peptides derived from thymosin $\beta_9$ following digestion with trypsin. The peptide fragments resulting from trypsin digestion of thymosin $\beta_9$ are designated T-1, T-1, T-2, T-3, T-4, T-6 and T-7 in Table III. The numbers in brackets in Tables I-III are assigned position of the designated fragment in the amino acid sequence of thymosin $\beta_8$ or thymosin $\beta_9$; while the numbers in parentheses are values obtained as predicted by the amino acid sequence of thymosin $\beta_8$ or thymosin $\beta_9$.

FIGS. I and II are composite diagrams of thymosin $\beta_8$ and thymosin $\beta_9$ sequences, respectively, and the peptide fragments thereof (represented by line segments) from the trypsin and Staph aureus protease digestion. Arrows pointing to the right in FIG. I indicate residues degraded sequentially by Edman's method. Arrows pointing to the left in FIG. II indicate the residues released by carboxypeptidase A (lysine only) followed by carboxypeptidase B (alanine and glutamine).

More particularly, Table I and FIG. I indicate that thymosin $\beta_8$ yielded 5 major tryptic peptides. Peptide T3 of thymosin $\beta_8$ contained lysine and had a COOH-terminal glutamine residue as determined by digestion with carboxypeptidase A. The terminal $Lys^{38}$-$Gln^{39}OH$ bond in thymosin $\beta_8$ was not cleaved by trypsin.

The sequences of peptides derived from thymosin $\beta_8$ were determined by manual Edman degradation, except for the blocked amino terminal peptide (peptide T5). This sequence was determined by digestion of T5 with Staph aureus proteinase V8, which yielded peptide T5S2, followed by mild acid hydrolysis, which yielded 2 equivalents of aspartic acid and one equivalent of alanine, plus a dipeptide, Lys-Pro, and a tripeptide, Leu-Gly-Glu, whose sequences were established by Edman degradation. Assignment of alanine to position 1 was also based on the fact that none of the other residues of T5S2 is known to occur as an acetylated $NH_2$-terminal residue in any proteins or in other peptides isolated from thymosin Fraction 5.

Digestion of thymosin $\beta_9$ with trypsin and separation of the tryptic peptides by HPLC yielded a pattern indistinguishable from that obtained with thymosin $\beta_8$. However, acid hydrolysis of peak T-1, isolated from tryptic digests of thymosin $\beta_9$, yielded the composition Ala(1), Lys(2), Glu(1), indicating the presence of glutamate and lysine residues that were not present in peak T-1 derived from thymosin $\beta_8$. Digestion of thymosin $\beta_9$ with Staph aureus protease yielded a tetrapeptide (designated S1 in FIG. II) with the composition, Glu(1), Lys(2), Ala(1), instead of the dipeptide Lys-Glu. Digestion of thymosin $\beta_9$ with carboxypeptidase B yielded 1.2 equivalents of lysine, and subsequent addition of carboxypeptidase A yielded Ala (1.2 equiv/mol), Lys (1.8 equiv/mol, total), Gln (1.3 equiv/mol) and Glu (0.2 equiv/mol). The results establish the terminal sequence of thymosin $\beta_9$. Peak T-1 derived from the tryptic digests, apparently contained both the tripeptide Glu-Ala-Lys from the COOH-terminus and the dipeptide Ala-Lys from positions 15 and 16. The results establish the terminal sequence of thymosin $\beta_9$ as the compound of Formula III.

TABLE I

Amino Acid Compositions of Thymosin $\beta_8$ and the Peptides Isolated Following Digestion with Trypsin

| Residue | $\beta_8$ | | T1 [15–16] | T2 [17–25] | T3 [32–39] | T4 [26–31] | T5 [1–14] | T5S1 [9–14] | T5S2 [1–8] | T5S2H1 | T5S2H2 |
|---|---|---|---|---|---|---|---|---|---|---|---|
| Asp | 4.6 | (5)[d] | | | | 0.9 (1) | 3.8 (4) | 1.8 (2) | 1.7 (2) | | |
| Thr | 3.8 | (5) | | 1.7 (2) | 0.9 (1) | 2.0 (2) | | | | | |
| Ser | 1.7 | (1) | | | 5.1 (5) | | 0.8 (1) | 0.9 (1) | | | |
| Glu | 9.0 | (9) | | 3.0 (3) | | | 1.2 (1) | | 1.1 (1) | | 0.9 (1) |
| Pro | 2.2 | (2) | | | | nd (1) | nd (1) | | nd (1) | 0.9 (1) | |
| Gly | 1.3 | (1) | | | | | 1.0 (1) | | 1.0 (1) | | 1.0 (1) |
| Ala | 2.2 | (2) | 1.0 (1) | | | | 1.1 (1) | | 1.3 (1) | | |
| Cys | 0 | (0) | | | | | | | | | |
| Val | 0.3 | (0) | | | | | | | | | |
| Met | 0.2 | (0) | | | | | | | | | |
| Ile | 1.8 | (2) | | | 0.9 (1) | | 1.0 (1) | 0.9 (1) | | | |
| Leu | 2.9 | (3) | | 1.0 (1) | | 1.0 (1) | 1.0 (1) | | 0.9 (1) | | 1.1 (1) |
| Tyr | 0.2 | (0) | | | | | | | | | |

TABLE I-continued

Amino Acid Compositions of Thymosin β8 and the Peptides Isolated Following Digestion with Trypsin

| Residue | β8 | | T1 [15–16] | T2 [17–25] | T3 [32–39] | T4 [26–31] | T5 [1–14] | T5S1 [9–14] | T5S2 [1–8] | T5S2H1 | T5S2H2 |
|---|---|---|---|---|---|---|---|---|---|---|---|
| Phe | 1.0 | (1) | | | | | 1.0 (1) | 1.1 (1) | | | |
| Lys | 8.3 | (8) | 1.0 (1) | 3.3 (3) | 1.2 (1) | 1.2 (1) | 2.2 (2) | 1.2 (1) | 1.1 (1) | 1.1 (1) | |
| His | 0.1 | (1) | | | | | | | | | |
| Arg | 0.3 | (0) | | | | | | | | | |
| nmol recovered | | | 45.2 | 50.2 | 42.3 | 57.8 | 39.2 | | | | |

TABLE II

Amino Acid Compositions of Peptides Formed from Thymosin β8 by Digestion with *Staph aureus* protease

| Residue | Peptides Isolated | | | | | |
|---|---|---|---|---|---|---|
| | S1 [38–39] | S2 [22–24] | S3 [14–21] | S4 [33–37] | S5 [25–32] | S6 [1–21] |
| Asp | | | | | 1.0 (1) | 4.3 (4) |
| Thr | | 0.9 (1) | 0.8 (1) | 0.9 (1) | 1.6 (2) | 0.6 (1) |
| Ser | | | | | | 1.2 (1) |
| Glu | 0.9 (1) | 2.1 (2) | 1.1 (1) | 2.9 (3) | 1.0 (1) | 2.1 (2) |
| Gly | | | | | | 1.4 (1) |
| Ala | | | 0.9 (1) | | | 2.1 (2) |
| Ile | | | | 1.2 (1) | | 1.2 (1) |
| Leu | | | 1.3 (1) | | 1.3 (1) | 2.1 (2) |
| Phe | | | | | | 1.2 (1) |
| Lys | 1.1 (1) | | 3.9 (4) | | 2.1 (2) | 4.7 (5) |
| nmol recovered | 4.6 | 5.2 | 1.9 | 4.6 | 4.6 | 4.1 |

TABLE III

Amino Acid Compositions of Thymosin β9 and Tryptic Peptides Derived From It

| Residue | β9 | | Tryptic Peptides | | | | Sum of Tryptic Peptides |
|---|---|---|---|---|---|---|---|
| | | | T-1'[a] | T-2 | T-6 | T-7 | |
| Asp | 4.6 | (5) | | | 1.13 (1) | 3.16 (4) | 5 |
| Thr | 3.03 | (5)[b] | | 1.93 (2) | 2.50 (3) | | 5 |
| Ser | 3.7 | (1)[b] | | | | 0.88 (1) | 1 |
| Glu | 10.6 | (9) | 1.01 (1) | 3.12 (3) | 4.24 (4) | 1.22 (1) | 9 |
| Gly | 1.2 | (1) | | | | 1.13 (1) | 1 |
| Ala | 2.1 | (3)[b] | 0.8 (1) | | | 2.03 (2) | 3 |
| Ile | 2.0 | (2) | | | 0.95 (1) | 1.00 (1) | 2 |
| Leu | 2.2 | (3)[b] | | 0.90 (1) | 1.06 (1) | 1.09 (1) | 3 |
| Phe | 1.1 | (1) | | | | 1.03 (1) | 1 |
| Lys | 8.5 | (9) | 1.19 (1) | 3.05 (3) | 2.13 (2) | 2.36 (3) | 9 |
| Pro | | | | | nd (1) | nd (1) | |
| Position in Sequence | | | [39–41] | [17–25] | [26–38] | [1–16] | |

| | Overlapping Tryptic Peptides | | |
|---|---|---|---|
| Residue | T-1 | T-3 | T-4 |
| Asp | | | 1.01 (1) |
| Thr | | 0.89 (1) | 1.75 (2) |
| Glu | | 3.89 (4) | |
| Ala | 0.8 (1) | | |
| Ile | | 0.84 (1) | |
| Leu | | | 1.02 (1) |
| Lys | 1.19 (1) | 1.37 (1) | 1.22 (1) |
| Pro | | | nd (1) |
| Position in Sequence | [15–16] | [32–38] | [26–31] |

[a]T-1 and T-1' emerged together. Presence of two peptides confirmed by carboxypeptidase analysis.
[b]Correct content of Thr, Ser, Ala and Leu confirmed by isolation and analysis of tryptic peptides.
nd = not determined.

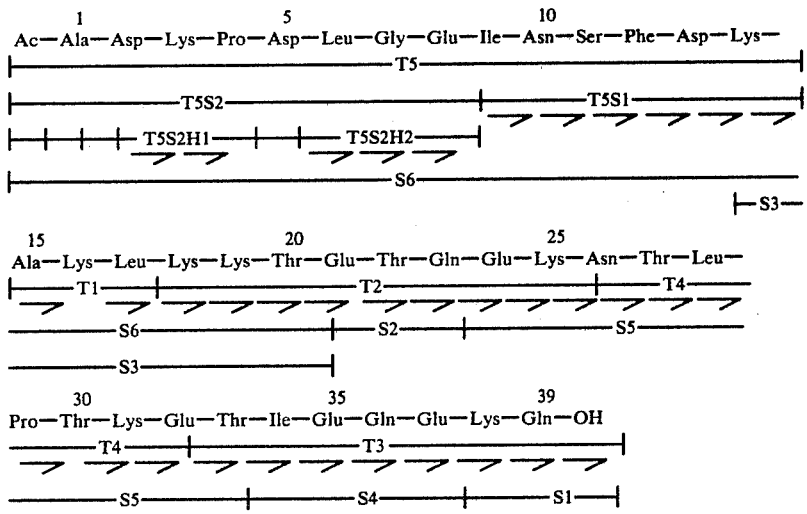

FIG. 1

```
        1                 5                    10
Ac—Ala—Asp—Lys—Pro—Asp—Leu—Gly—Glu—Ile—Asn—Ser—Phe—Asp—Lys—
   |————————————————————————T5————————————————————————|
   |————————————T5S2————————————————|————T5S1————|
   |—|—|—|—T5S2H1—|—|— T5S2H2——|
   |————————————————————S6————————————————————————|   |—S3—|

15                20                  25
   Ala—Lys—Leu—Lys—Lys—Thr—Glu—Thr—Gln—Glu—Lys—Asn—Thr—Leu—
   |——T1——|————————T2————————|————T4———
   —————S6—————————|———S2———|———S5————
   ————S3————————|

30              35            39
   Pro—Thr—Lys—Glu—Thr—Ile—Glu—Gln—Glu—Lys—Gln—OH
   ————T4————|—————————T3—————————|
   ————S5————|————S4————|——S1——|
```

FIG. II

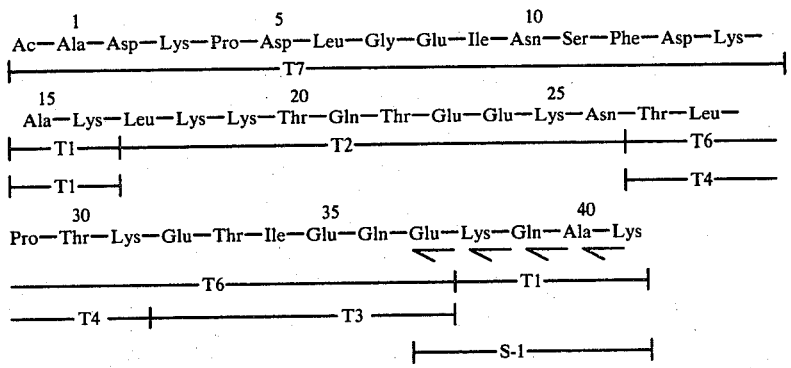

Also included within the scope of the present invention are the pharmaceutically acceptable salts of compounds of formula I, such as sodium or potassium or with strong organic bases such as guanidine. In addition, the counter ions of these cations as well as of lysine residues in compounds of formula I, such as the hydrochloride, hydrobromide sulfate, phosphate, maleate, acetate, citrate, benzoate, succinate, malate, ascorbate and the like, may be included in the preparation.

The compounds of formula I of the present invention have activity in the restoration and stimulation of immune function. Thus, they are useful, for example, in the treatment of opportunistic infections in an immunosuppressed subject when administered to the subject in an immunopotentiating effective amount. Such activity must be considered unexpected in view of the knowledge in the peptide hormone art that the deletion of even one amino acid from the sequence of a biologically active peptide may result in the loss of biological activity.

The compounds of formula I and salts thereof may be used as medicaments, for example, in the form of pharmaceutical preparation which contain them in association with a compatible pharmaceutical carrier material. This carrier material can be sterile water or saline suitable for parenteral administration (e.g. intravenous, subcutaneous or intramuscular). The pharmaceutical preparations may be subjected to conventional pharmaceutical operations, such as sterilization and may contain conventional adjuvants, such as preservatives, stabilizers, wetting agent and the like.

The pharmaceutical preparations can be prepared according to methods well known in the art. They can be administered parenterally from once a day up to four times a day. The parenteral dosage form preferably contains 10 ng-100 µg of active ingredient per kg of body weight.

The compounds of formula I were tested for protective activity against opportunistic infections in immunosuppressed mice. Female ddY mice (6 weeks old) weighing about 25 g were pretreated daily for eight days with 5-fluorouracil (5-FU) (25 mg/kg/day, i.p.) and with thymosin α₁ or with compounds of formula I (i.p.) at varying dosages. The mice were then infected with Candida albicans ATCC 10231 (1×10⁵ cells or more) at 24 hours after the last treatment. One control group was administered 5-FU and saline solution and a second control group received neither 5-FU nor a thymic polypeptide prior to infection with Candida albicans. The number of animals surviving eight days after infection with Candida albicans and 15 days after infection with Candida albicans is presented in Table IV.

As can be seen from Table IV, treatment with 5-FU made the mice susceptible to the infection with Candida albicans, while the control group which did not receive 5-FU pretreatment was highly resistant to infection. The protective effects against infection which were conferred by the compounds of formula I were comparable to the protective effects conferred by thymosin $\alpha_1$.

TABLE IV

|  | Dose µg/kg/day i.p. | Survivors at Day 8 | Day 15 | P* |
| --- | --- | --- | --- | --- |
| Thymosin $\alpha_1$ | 4 | 7/10 | 6/10 | 0.0001 |
|  | 40 | 7/10 | 7/10 | <0.0001 |
| Thymosin $\beta_4$ | 0.4 | 7/10 | 6/10 | <0.0001 |
|  | 4 | 5/10 | 5/10 | 0.0007 |
|  | 40 | 1/10 | 1/10 |  |
| Thymosin $\beta_8$ | 0.4 | 9/9 | 9/9 | <0.0001 |
|  | 4 | 8/9 | 8/9 | <0.0001 |
|  | 40 | 7/9 | 7/9 | <0.0001 |
| Thymosin $\beta_9$ | 0.04 | 4/10 | 4/10 | <0.003 |
|  | 0.4 | 7/10 | 6/10 | <0.0001 |
|  | 4 | 3/10 | 3/10 | <0.003 |
|  | 40 | 4/10 | 4/10 | <0.004 |
| Control (5-FU) |  | 10/10 | 10/10 |  |
| Control |  | 1/10 | 1/10 |  |

*Rank sum test

The following examples further elucidate the invention but are not meant to restrict the invention in scope or spirit.

EXAMPLE 1

Preparation of thymosin $\beta_8$:

A sample of thymosin Fraction 5 (1.2 g) was dissolved in 100 ml of 2% ampholine for separation in the pH range 4–6 and filtered through a 0.45 µm molecular pore filter. After addition of 4 g of Ultrodex the gel was cast onto a glass plate (11×24.5 cm) and electrofocused for 16 h over the long direction at 8° C. and 8 W, maintaining the voltage below 1.5 kV and a current below 20 mA. The focused gel was cut with a grid into 30 sections, each of which was eluted on a small column with 5 ml of H₂O. The pH of eluate was determined at 0° C. For analysis by HPLC 5 µl aliquots of each eluate were applied to a RP18 column (5µ, 4.6×250 mm) equilibrated with 0.2 M pyridine-1 M formic acid, containing 0.05% thiodiglycol (v/v) at a flow rate of 0.7 ml/min. The peptides were eluted with the same buffer containing n-propanol, the concentration of which was increased by 4% every 10 min to a final concentration of 40% (v/v). At 10 s intervals 5 µl samples were diverted to the fluorescamine detector. For the preparative runs, twelve 450 µl aliquots of the eluates from slices 12-15 were injected successively onto the same RP-18 column used for the analytical runs and the peptides eluted with the same buffer and n-propanol gradient. Fractions (0.7 ml) were collected every 2 min and aliquots (5 µl of a 1:25 dilution) of each aliquot analyzed by direct injection into the borate buffer line of the fluorescamine detector, because the automatic column monitoring was off-scale. Fractions found to contain the peptides corresponding to thymosin $\beta_4$ and thymosin $\beta_8$ were separately pooled and lyophilized.

EXAMPLE 2

Digestion of thymosin $\beta_8$:

Digestion with trypsin was carried out in 200 µl volumes containing 312 mg of thymosin $\beta_8$ and 20 µg of trypsin in 0.4 M pyridine, pH 7.5. After 14 hours (h) at room temperature the reactions were terminated by the addition of 15.2 µl of concentrated HCOOH and injected onto the reverse phase column, followed by 0.2 M pyridine-1 M formic acid at a flow rate of 0.37 ml/min. Elution was with a gradient of $CH_3CN$, increasing from 0 to 40% (v/V) over a period of 2 hours (h). Aliquots (5 µl) were diverted to the fluorescamine detection system every 20 seconds (s). Fractions were collected every 2 min. The major peaks were collected and analyzed. The minor peaks were identified as products of incomplete digestion.

Digestion of thymosin $\beta_8$ with *Staph aureus* Protease V8 was carried out in 40 µl reaction mixtures containing 0.1 M $NH_4HCO_3$, pH 7.8, 2 mM EDTA and a ratio of peptide to protease of 30:1 (w/w). After incubation for 14 h at 25° C. the solutions were diluted to 400 µl with 0.2 M pyridine—1 M formic acid and the peptides separated on an RP18 column. In this experiment 6.98 µmol of peptide was digested.

The peptides derived from digestion with trypsin and the *Staph aureus* protease V8 were isolated and analyzed by HPLC.

EXAMPLE 3

Preparation of thymosin $\beta_9$:

Calf thymus collected at the time of slaughter was cut into 60 g pieces and immediately frozen in liquid $N_2$ and stored in liquid $N_2$. The frozen tissue was pulverized and the frozen powder added with mechanical stirring to nine volumes of ice-cold 6 M guanidine hydrochloride solution. The suspension was then blended at high speed in a large Waring blender. This suspension was then treated with pyridine to a final concentration of 0.2 M and with formic acid to a final concentration of 1 M. The suspended material was removed by centrifugation and the supernatant solution filtered successively through Whatman No. 541 and Whatman No. 1 filters. The clear solution was pumped through a hollow fiber concentration system, having a HIP10 cartridge. The ultrafiltrate emerging from the hollow fiber system was pumped onto a prepackaged reverse phase column [RP8, 40-63 µm] at a rate of flow balanced against that of the effluent from the hollow fiber system. The effluent from the column was returned for recycling to the reservoir feeding the DC2 hollow fiber system. Adsorption of peptides was determined by analysis on HPLC of aliquots solution emerging in the HIP10 ultrafiltrate. When adsorption was complete, the RP8 column was washed with 0.4 M pyridine-0.5 M formic acid (pH 4.0) to remove salts and the peptides were eluted with 40% n-propanol in 0.4 M pyridine-0.5 M formic acid, pH 4.0. The quantity of eluting solution was approximately 350 ml for each 100 g of thymus tissue extracted. The solution contains the eluted peptides thymosin $\beta_9$ and thymosin $\beta_4$. This solution was lyophlized and stored as dry powder.

To separate thymosin $\beta_4$ from thymosin $\beta_9$, advantage was taken of the presence of methionine in the former. The 40% propanol eluate from the RP8 column which had been lyophilized was dissolved in 5 ml of 0.2 M pyridine-1 M HCOOH and oxidized for 45 minutes at room temperature with one-half volume of 30% $H_2O_2$. The sulfoxide form of thymosin $\beta_4$ was separated from thymosin $\beta_9$ by HPLC utilizing a reverse phase C18 hydrophobic resin and eluting the resin with a gradient of increasing concentrations of n-propanol from 0 to 40% by volume in a 0.2 M pyridine-1 M formic acid buffer solution of about pH 4.0. In this HPLC process thymosin $\beta_9$ emerges after the sulfoxide form of thymosin $\beta_4$.

Based on the results of the direct analysis of aliquots from several different preparations the quantity of thymosin $\beta_9$ yield was 8–18 µg/g tissue.

EXAMPLE 4

Digestion of thymosin $\beta_9$:

Digestion with trypsin was carried out following the procedure of Example 2, substituting thymosin $\beta_9$ for thymosin $\beta_8$.

What is claimed is:

1. Polypeptides essentially free of other proteinacious material and having the following amino acid sequence:

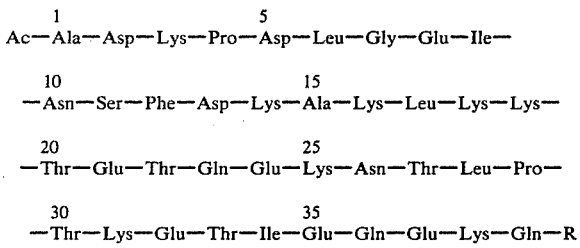

wherein Ac represents N-acetyl and R represents —OH or —Ala—Lys—OH
and the pharmaceutically acceptable acid addition salts or base salts thereof.

2. A polypeptide according to claim 1 having the following amino acid sequence:

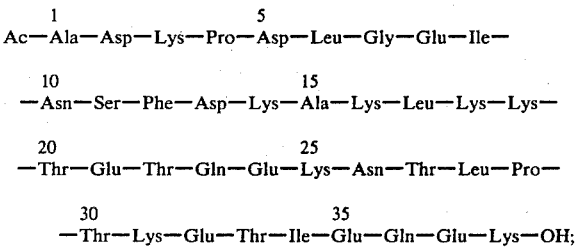

3. A polypeptide according to claim 1 having the following amino acid sequence:

```
              1                  5
       Ac—Ala—Asp—Lys—Pro—Asp—Leu—Gly—Glu—Ile—

10                       15
       —Asn—Ser—Phe—Asp—Lys—Ala—Lys—Leu—Lys—Lys—

20                  25
       —Thr—Glu—Thr—Gln—Glu—Lys—Asn—Thr—Leu—Pro—
```

-continued
```
              30                  35
       —Thr—Lys—Glu—Thr—Ile—Glu—

40
                 Gln—Glu—Lys—Gln—Ala—Lys—OH;
```

4. A method for preventing and treating opportunistic infections in immunosuppressed subjects, which method comprises administering to the subject an immunopotentiating effective amount of a compound of formula I of claim 1.

* * * * *